United States Patent [19]
Sharkey et al.

[11] Patent Number: 6,099,514
[45] Date of Patent: *Aug. 8, 2000

[54] METHOD AND APPARATUS FOR DELIVERING OR REMOVING MATERIAL FROM THE INTERIOR OF AN INTERVERTEBRAL DISC

[75] Inventors: Hugh R. Sharkey, Woodside; John Ashley, San Francisco; Joel Saal; Jeffrey A. Saal, both of Portola Valley; Le Trong Le, San Jose, all of Calif.

[73] Assignee: Oratec Interventions, Inc., Menlo Park, Calif.

[*] Notice: This patent is subject to a terminal disclaimer.

[21] Appl. No.: 09/162,704

[22] Filed: Sep. 29, 1998

Related U.S. Application Data

[60] Provisional application No. 60/047,820, May 28, 1997, provisional application No. 60/047,841, May 28, 1997, provisional application No. 60/047,818, May 28, 1997, provisional application No. 60/047,848, May 28, 1997, provisional application No. 60/045,941, May 28, 1997, and provisional application No. 60/029,734, Oct. 23, 1996.

[51] Int. Cl.$^7$ .................................................. A61M 5/00
[52] U.S. Cl. ...................................... 604/264; 604/95.01
[58] Field of Search .................................. 604/523–529, 604/264, 93, 164, 22, 95

[56] References Cited

U.S. PATENT DOCUMENTS

| | | | |
|---|---|---|---|
| 2,090,923 | 8/1937 | Wappler | 128/303.15 |
| 3,178,728 | 4/1965 | Christensen | 3/1 |
| 3,579,643 | 5/1971 | Morgan | 3/1 |
| 3,776,230 | 12/1973 | Neefe | 128/260 |
| 3,807,390 | 4/1974 | Ostrowski et al. | 604/523 |

(List continued on next page.)

FOREIGN PATENT DOCUMENTS

| | | | |
|---|---|---|---|
| 0 257 116 A1 | 3/1988 | European Pat. Off. | A61N 1/36 |
| 0 274 705 A1 | 7/1988 | European Pat. Off. | A61M 23/00 |
| 0 479 482 A1 | 4/1992 | European Pat. Off. | A61B 17/39 |
| 0 521 595 A2 | 1/1993 | European Pat. Off. | A61M 25/01 |
| 0 542 412 A1 | 5/1993 | European Pat. Off. | A61B 17/39 |

(List continued on next page.)

OTHER PUBLICATIONS

Sharkey, H. et al., "Method and Apparatus for Treating Intervertebral Discs with Thermal Energy", U.S. Patent application Ser. No. 08/881,525, filed Jun. 24, 1997. (766).

Sharkey, H. et al., "Method and Apparatus for Treating Intervertebral Discs with Electromagnetic Energy", U.S. Patent application Ser. No. 08/881,692 filed Jun. 24, 1997. (767).

(List continued on next page.)

Primary Examiner—Wynn Wood Coggins
Assistant Examiner—Deborah Blyveis
Attorney, Agent, or Firm—David J. Weitz; Wilson Sonsini Goodrich & Rosati

[57] ABSTRACT

An externally guidable intervertebral disc apparatus manipulates disc tissue present at a selected location of an intervertebral disc, comprising a catheter having a distal end, a proximal end, and a longitudinal axis, the catheter having an intradiscal section at the distal end of the catheter, the intradiscal section being extendible into the disc, having sufficient rigidity to be advanceable through the nucleus pulposus of the disc under a force applied longitudinally to the proximal end, having sufficient flexibility in a direction of the disc plane to be compliant with the inner wall, having insufficient penetration ability to be advanceable through the inner wall of the annulus fibrosus under the applied force; and a functional element located in the intradiscal section for adding or removing energy or a material at the selected location of the disc. Methods of using the apparatus are also disclosed.

29 Claims, 8 Drawing Sheets

U.S. PATENT DOCUMENTS

| | | | |
|---|---|---|---|
| 3,856,015 | 12/1974 | Iglesias | 128/303.15 |
| 3,867,728 | 2/1975 | Substad et al. | 3/1 |
| 3,879,767 | 4/1975 | Substad | 3/1 |
| 3,886,600 | 6/1975 | Kahn et al. | 3/1 |
| 3,938,198 | 2/1976 | Kahn et al. | 3/1.912 |
| 3,945,375 | 3/1976 | Banko | 128/6 |
| 3,987,499 | 10/1976 | Scharbach et al. | 3/1.91 |
| 3,992,725 | 11/1976 | Homsy | 3/1 |
| 4,043,342 | 8/1977 | Morrison, Jr. | 128/303.14 |
| 4,085,466 | 4/1978 | Goodfellow et al. | 3/1.91 |
| 4,129,470 | 12/1978 | Homsy | 156/155 |
| 4,134,406 | 1/1979 | Iglesias | 128/303.15 |
| 4,224,696 | 9/1980 | Murray et al. | 3/1.911 |
| 4,224,697 | 9/1980 | Murray et al. | 3/1.911 |
| 4,326,529 | 4/1982 | Doss et al. | 128/303.1 |
| 4,344,193 | 8/1982 | Kenny | 3/1.911 |
| 4,362,160 | 12/1982 | Hiltebrandt | 128/303.15 |
| 4,375,220 | 3/1983 | Matvias | 128/804 |
| 4,381,007 | 4/1983 | Doss | 128/303.1 |
| 4,397,314 | 8/1983 | Vaguine | 128/399 |
| 4,405,314 | 9/1983 | Cope | 604/51 |
| 4,476,862 | 10/1984 | Pao | 128/303.17 |
| 4,483,338 | 11/1984 | Bloom et al. | 128/303.13 |
| 4,517,965 | 5/1985 | Ellison | 128/20 |
| 4,517,975 | 5/1985 | Garito et al. | 128/303.13 |
| 4,590,934 | 5/1986 | Malis et al. | 128/303.14 |
| 4,593,691 | 6/1986 | Lindstrom et al. | 128/303.14 |
| 4,597,379 | 7/1986 | Kihn et al. | 128/1 R |
| 4,601,705 | 7/1986 | McCoy | 604/94 |
| 4,651,734 | 3/1987 | Doss et al. | 128/303.14 |
| 4,737,146 | 4/1988 | Amaki et al. | 604/51 |
| 4,811,733 | 3/1989 | Borsanyi et al. | 128/303.14 |
| 4,815,462 | 3/1989 | Clark | 128/305 |
| 4,838,859 | 6/1989 | Strassmann | 604/95 |
| 4,846,175 | 7/1989 | Frimberger | 128/303.15 |
| 4,873,976 | 10/1989 | Schreiber | 128/334 R |
| 4,894,063 | 1/1990 | Nashef | 623/13 |
| 4,895,148 | 1/1990 | Bays et al. | 606/213 |
| 4,907,585 | 3/1990 | Schachar | 606/28 |
| 4,907,589 | 3/1990 | Cosman | 606/34 |
| 4,924,865 | 5/1990 | Bays et al. | 606/77 |
| 4,944,727 | 7/1990 | McCoy | 604/95 |
| 4,950,234 | 8/1990 | Fujioka et al. | 604/60 |
| 4,955,882 | 9/1990 | Hakky | 606/14 |
| 4,966,597 | 10/1990 | Cosman | 606/50 |
| 4,976,709 | 12/1990 | Sand | 606/5 |
| 4,976,715 | 12/1990 | Bays et al. | 606/77 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,085,657 | 2/1992 | Ben-Simhon | 606/42 |
| 5,098,430 | 3/1992 | Fleenor | 606/42 |
| 5,100,402 | 3/1992 | Fan | 606/41 |
| 5,103,804 | 4/1992 | Abele et al. | 128/4 |
| 5,114,402 | 5/1992 | McCoy | 604/95 |
| 5,129,889 | 7/1992 | Hahn et al. | 604/265 |
| 5,152,748 | 10/1992 | Chastagner | 604/95 |
| 5,178,620 | 1/1993 | Eggers et al. | 606/41 |
| 5,186,181 | 2/1993 | Franconi et al. | 128/804 |
| 5,191,883 | 3/1993 | Lennox et al. | 128/401 |
| 5,192,267 | 3/1993 | Shapira et al. | 604/22 |
| 5,201,729 | 4/1993 | Hertzmann et al. | 606/2 |
| 5,201,730 | 4/1993 | Easley et al. | 606/4 |
| 5,201,731 | 4/1993 | Hakky | 606/15 |
| 5,213,097 | 5/1993 | Zeindler | 128/401 |
| 5,230,334 | 7/1993 | Klopotek | 128/399 |
| 5,242,439 | 9/1993 | Larsen et al. | 606/15 |
| 5,242,441 | 9/1993 | Avitall | 606/41 |
| 5,261,906 | 11/1993 | Pennino et al. | 606/46 |
| 5,267,994 | 12/1993 | Gentelia et al. | 606/15 |
| 5,275,151 | 1/1994 | Shockey et al | 128/4 |
| 5,279,559 | 1/1994 | Barr | 604/95 |
| 5,284,479 | 2/1994 | de Jong | 604/60 |
| 5,304,169 | 4/1994 | Sand | 606/5 |
| 5,308,311 | 5/1994 | Eggers et al. | 606/28 |
| 5,311,858 | 5/1994 | Adair | 128/4 |
| 5,320,115 | 6/1994 | Kenna | 128/898 |
| 5,323,778 | 6/1994 | Kandarpa et al. | 128/653.2 |
| 5,334,193 | 8/1994 | Nardella | 606/41 |
| 5,342,357 | 8/1994 | Nardella | 606/40 |
| 5,345,945 | 9/1994 | Hodgson et al. | 128/772 |
| 5,348,554 | 9/1994 | Imran et al. | 606/41 |
| 5,352,868 | 10/1994 | Denen et al. | 219/501 |
| 5,354,331 | 10/1994 | Schachar | 623/4 |
| 5,364,395 | 11/1994 | West, Jr. | 606/46 |
| 5,366,443 | 11/1994 | Eggers et al. | 604/114 |
| 5,366,490 | 11/1994 | Edwards et al. | 607/99 |
| 5,382,247 | 1/1995 | Cimino et al. | 606/33 |
| 5,389,100 | 2/1995 | Bacich et al. | 606/108 |
| 5,397,304 | 3/1995 | Truckai | 604/95 |
| 5,401,272 | 3/1995 | Perkins | 606/15 |
| 5,415,633 | 5/1995 | Lazarus et al. | 604/95 |
| 5,423,806 | 6/1995 | Dale et al. | 606/15 |
| 5,433,739 | 7/1995 | Sluijter et al. | 607/99 |
| 5,437,661 | 8/1995 | Rieser | 606/15 |
| 5,437,662 | 8/1995 | Nardella | 606/40 |
| 5,451,223 | 9/1995 | Ben-Simhon | 606/42 |
| 5,458,596 | 10/1995 | Lax et al. | 606/31 |
| 5,465,737 | 11/1995 | Schachar | 128/898 |
| 5,484,403 | 1/1996 | Yoakum et al. | 604/59 |
| 5,484,432 | 1/1996 | Sand | 606/5 |
| 5,484,435 | 1/1996 | Fleenor et al. | 606/46 |
| 5,487,757 | 1/1996 | Truckai et al. | 607/122 |
| 5,498,258 | 3/1996 | Hakky et al. | 606/15 |
| 5,500,012 | 3/1996 | Brucker et al. | 607/122 |
| 5,507,812 | 4/1996 | Moore | 623/13 |
| 5,514,130 | 5/1996 | Baker | 606/41 |
| 5,524,338 | 6/1996 | Martyniuk et al. | 29/825 |
| 5,527,331 | 6/1996 | Kresch et al. | 606/170 |
| 5,542,920 | 8/1996 | Cherif Cheikh | 604/57 |
| 5,569,242 | 10/1996 | Lax et al. | 606/42 |
| 5,599,346 | 2/1997 | Edwards et al. | 606/41 |
| 5,630,839 | 5/1997 | Corbett, III et al. | 607/137 |
| 5,681,282 | 10/1997 | Eggers et al. | 604/114 |
| 5,686,366 | 11/1997 | Eggers et al. | 604/114 |
| 5,688,270 | 11/1997 | Yates et al. | 606/51 |
| 5,697,909 | 12/1997 | Eggers et al. | 604/114 |
| 5,718,702 | 2/1998 | Edwards | 606/41 |
| 5,782,795 | 7/1998 | Bays | 604/22 |

FOREIGN PATENT DOCUMENTS

| | | | |
|---|---|---|---|
| 0 558 297 A2 | 9/1993 | European Pat. Off. | A61M 25/00 |
| 0 566 450 A1 | 10/1993 | European Pat. Off. | A61N 5/02 |
| 0 572 131 A1 | 12/1993 | European Pat. Off. | A61B 17/39 |
| 0 682 910 A1 | 11/1995 | European Pat. Off. | A61B 1/00 |
| 0 479 482 B1 | 5/1996 | European Pat. Off. | A61B 17/39 |
| 0 729 730 A1 | 9/1996 | European Pat. Off. | A61B 17/32 |
| 0 737 487 A2 | 10/1996 | European Pat. Off. | A61M 25/01 |
| 0 783 903 A1 | 7/1997 | European Pat. Off. | A61N 5/04 |
| 1122634 | 9/1956 | France . | |
| 3511107A1 | 2/1986 | Germany | A61B 17/39 |
| 3632197A1 | 3/1988 | Germany | A61B 10/00 |
| 5-42166 | 5/1993 | Japan | A61B 17/39 |
| 637118 | 12/1978 | U.S.S.R. | A61B 17/18 |
| 1 340 451 | 12/1973 | United Kingdom | A61F 1/00 |
| 2 164 473 | 3/1986 | United Kingdom | A61B 17/36 |
| WO 85/02762 | 7/1985 | WIPO | A61B 17/36 |
| WO 92/05828 | 4/1992 | WIPO | A61M 25/00 |
| WO 92/10142 | 6/1992 | WIPO | A61B 17/36 |
| WO 93/01774 | 2/1993 | WIPO | A61F 7/12 |
| WO 93/20984 | 10/1993 | WIPO | B26D 1/11 |
| WO 95/01814 | 1/1995 | WIPO | A61N 5/02 |

| | | | |
|---|---|---|---|
| WO 95/13113 | 5/1995 | WIPO | A61N 5/02 |
| WO 95/18575 | 7/1995 | WIPO | A61B 17/39 |
| WO 95/20360 | 8/1995 | WIPO | A61B 17/39 |
| WO 95/30373 | 11/1995 | WIPO | A61B 17/00 |
| WO 96/34568 | 7/1996 | WIPO | A61B 17/36 |
| WO 96/32885 | 10/1996 | WIPO | A61B 5/04 |
| WO 96/34559 | 11/1996 | WIPO | A61B 5/0402 |
| WO 96/39914 | 12/1996 | WIPO | A61B 1/00 |
| WO 97/06855 | 2/1997 | WIPO | A61N 1/40 |
| WO 98/07468 | 2/1998 | WIPO | A61N 1/40 |
| WO 98/17190 | 4/1998 | WIPO | A61B 18/00 |

OTHER PUBLICATIONS

Sharkey, H. et al., "Method and Apparatus for Delivering or Removing Material from the Interior of an Intervertebral Disc", U.S. Patent application Ser. No. 08/881,527, filed Jun. 28, 1997. (768).

Sharkey, H. et al., "Method and Apparatus for Treating Annular Fissures in Intervertebral Discs", U.S. Patent application Ser. No. 08/881,693, filed Jun. 24, 1997. (769).

Sharkey, H. et al., "Method and Apparatus for Treating Intervertebral Disc Degeneration", U.S. Patent application Ser. No. 08/881,694, filed Jun. 24, 1997. (770).

Sharkey, H. et al., "Method and Apparatus for Treating Annular Fissures in Intervertebral Discs", U.S. Patent application Ser. No. 09/153,552, filed Sep. 15, 1998. (804).

Christian, C. et al., "Allograft Anterior Cruciate Ligament Reconstruction with Patellar Tendon: An Endoscopic Technique", *Operative Techniques in Sports Medicine,* vol. 1, No. 1, Jan. 1993, pp. 50–57.

Houpt, J. et al., "Experimental Study of Temperature Distributions and Thermal Transport During Radiofrequency Current Therapy of the Intervertebral Disc", *SPINE,* vol. 21, No. 15, (1996), pp.1808–1813.

Troussier, B. et al., "Percutaneous Intradiscal Radio–Frequency Thermocoagulation: A Cadaveric Study", *SPINE,* vol. 20, No. 15, (Aug. 1995), pp. 1713–18.

Beadling, L., "Bi–Polar electrosurgical devices: Sculpting the future of arthroscopy", *Orthopedics today,* vol. 17, No. 1, Jan. 1997, 4 pages.

Ellman International Mfg., Inc., 1989, Catalog, pp. 1–15, 20.

Cosset, J.M., Resistive Radiofrequency (Low Frequency) Interstitial Heating (RF Technique), Interstitial Hyperthermia, Dec. 6, 1993, pp. 3–5, 37.

Attachment I: Competitive Literature on Generators with Bipolar Capabilities, IME Co., Ltd., pp. 60–86.

Attachment II: Competitive Literature on Bipolar Forceps and Footswitch Controls, IME Co., Ltd. pp. 87–104.

Auhll, Richard A., "The Use of the Resectoscope in Gynecology." Biomedical Business International Oct. 11, 1990, pp. 91–93.

METHOD AND APPARATUS FOR DELIVERING OR REMOVING MATERIAL FROM THE INTERIOR OF AN INTERVERTEBRAL DISC

REFERENCES TO PARENT AND CO-PENDING APPLICATIONS

This application claims priority to U.S. application Ser. No. 09/153,552 filed Sep. 15, 1998, U.S. application Ser. Nos. 08/881,525, 08/881,527, 08/881,692, 08/881,693, 08/881,694 filed Jun. 24, 1997, which each claims priority to U.S. Provisional Application Nos. 60/047,820, 60/047,841, 60/047,818, 60/047,848 filed May 28, 1997, U.S. Provisional Application No. 60/045,941 filed May 28, 1997, and U.S. Provisional Application Nos. 60/029,734, 60/029,735, 60/029,600, 60/029,602 filed Oct. 23, 1996. Application Serial Nos. 08/881,525, 08/881,692, 08/881,693, 08/881, 694, 60/029,734, 60/045,941 are each incorporated herein by reference.

BACKGROUND

1. Field of the Invention

This invention relates to methods and apparatuses for inspection and modification of intervertebral disc tissue and more particularly to the diagnosis and treatment of intervertebral disc problems using percutaneous disc techniques without the need for major surgical intervention.

2. Description of Related Art

Intervertebral disc abnormalities have a high incidence in the population and may result in pain and discomfort if they impinge on or irritate nerves. Disc abnormalities may be the result of trauma, repetitive use, metabolic disorders and the aging process and include such disorders but are not limited to (i) localized tear or fissure in the annulus fibrosus, (ii) localized disc herniations with contained or escaped extrusions, and (iii) chronic, circumferential bulging discs.

Disc fissures occur result from structural degeneration (a part of the aging process that may be accelerated by trauma) of fibrous components of the annulus fibrosus. Sneezing, bending or just attrition can separate these degenerated annulus fibers, creating a fissure. The fissure may or may not be accompanied by extrusion of nucleus pulposus material into or beyond the annulus fibrosus. The fissure itself may be the sole morphological change, above and beyond the generalized degenerative changes in the connective tissue of the disc. Due the fissure, biochemicals may escape from the disc and irritate surrounding structures. Disc fissures can be debilitatingly painful. The fissure may also be associated with a herniation of that portion of the wall.

With a contained disc herniation, the nucleus pulposus may work its way partly through the annulus and there are no free disc fragments in the spinal canal. Nevertheless, this is problematic because the outward protrusion can press on the spinal nerves or irritate other structures.

Another disc problem occurs when the disc bulges out circumferentially in all directions and not just in one location. This occurs when over time, the disc weakens, bulges and takes on a "roll" shape. Mechanical stiffness of the joint is reduced and the joint may become unstable. One vertebra may eventually settle on top of another. This problem continues as the body ages and accounts for shortened stature in old age. With the increasing life expectancy of the population, such degenerative disc disease and impairment of nerve function are becoming major public health problems. As the disc "roll" extends beyond the normal circumference, the disc height may be compromised, foramina with nerve roots are compressed. In addition, osteophytes may form on the outer surface of the disc roll and further encroach upon the spinal canal and for the nerve foramina. This condition is called lumbar spondylosis.

It has been thought that disc degeneration creates pain predominantly via segmental instability which disturbs sensitive structures which register pain. Traditional, conservative methods of treatment include bed rest, pain and muscle relaxant medication, physical therapy or steroid injection. Upon failure of conservative therapy, spinal pain (assumed to be due to instability) has been treated by spinal fusion, with or without instrumentation, which causes the vertebrae above and below the disc to grow solidly together and form a single, solid piece of bone. The procedure is carried out with or without discectomy. Other treatments include discectomy alone or disc decompression with or without fusion. Other methods include laminectomy or percutaneous nuclectomy to reduce pressure on the annulus by removing some of the interior nucleus pulposus. Surgical complications include disc space infection, nerve root injury, hematoma formation, instability of the adjacent vertebrae and collapse of the disc from further decrease in height.

These interventions have been problematic in that alleviation of back pain is unpredictable even if surgery appears successful. In attempts to overcome these difficulties, new devices have been introduced to the market, including but not limited to pedicle screws and interbody fusion cages. Although pedicle screws provide a high fusion success rate, there is still no direct correlation between fusion success rate and patient improvement in function and pain. Studies on fusion have demonstrated success rates of between 50% and 67% for pain improvement, and a significant number of patients have more pain postoperatively. Therefore, different methods of helping patients with degenerative disc problems need to be explored.

FIGS. 1(a) and 1(b) illustrate a cross-sectional anatomical view of a vertebra and associated disc and a lateral view of a portion of a lumbar and thoracic spine, respectively. Structures of a typical cervical vertebra (superior aspect) are shown in FIG. 1(a): 104—lamina; 106—spinal cord; 108—dorsal root of spinal nerve; 114—ventral root of spinal nerve; 116—posterior longitudinal ligament; 118—intervertebral disc; 120—nucleus pulposus; 122—annulus fibrosus; 124—anterior longitudinal ligament; 126—vertebral body; 128—pedicle; 130—vertebral artery; 132—vertebral veins; 134—superior articular facet; 136—posterior lateral portion of the annulus; 138—posterior medial portion of the annulus; and 142—spinous process. FIG. 1(b) is a lateral aspect of the lower portion of a typical spinal column showing the entire lumbar region and part of the thoracic region and displaying the following structures: 118—intervertebral disc; 126—vertebral body; 142—spinous process; 170—inferior vertebral notch; 110—spinal nerve; 174—superior articular process; 176—lumbar curvature; and 180—sacrum.

The presence of the spinal cord and the posterior portion of the vertebral body, including the spinous process, and superior and inferior articular processes, prohibit introduction of a needle or trocar from a directly posterior position. This is important because the posterior disc wall is the site of symptomatic annulus fissures and disc herniations and protrusions/extrusions that compress or irritate spinal nerves for most degenerative disc syndromes. The inferior articular process 168, along with the pedicle 128 and the lumbar spinal nerve 110, form a small "triangular" window (shown in black in FIG. 1(c)) through which introduction can be achieved from the posterior lateral position. FIG. 1(d) is a cross-sectional view of the lower back with an instrument introduced by the posterior lateral approach.

It is well known to those skilled in the art that percutaneous access to the disc is achieved by placing an introducer into the disc from this posterior lateral approach, but the triangular window does not allow much room to maneuver. Once the introducer pierces the tough annulus fibrosus, the introducer is fixed at two points along its length and has very little freedom of movement. Thus, this approach has allowed access only to small portions of the central and anterior nucleus pulposus. Current methods do not permit percutaneous access to the posterior half of the nucleus or to the posterior wall of the disc. Major and potentially dangerous surgery would be required to access these areas.

U.S. Pat. No. 5,433,739 (the "'739 patent") discloses placement of an RF electrode in an interior region of the disc approximately at the center of the disc. RF power is applied, and heat then putatively spreads out globally throughout the disc. The '739 patent teaches the use of a rigid shaft which includes a sharpened distal end that penetrates through the annulus fibrosus and into the nucleus pulposus. In one embodiment the shaft has to be rigid enough to permit the distal end of the RF electrode to pierce the annulus fibrosus, and the ability to maneuver its distal end within the nucleus pulposus is limited. In another embodiment, a somewhat more flexible shaft is disclosed. However, the embodiments of the '739 patent do not permit access to the posterior, posterior lateral and posterior medial region of the disc; nor do they provide for delivery of material to treat the annulus, nor do the embodiments permit temperature monitoring at the posterior annulus.

U.S. Pat. No. 5,201,729 (the "'729 patent") discloses the use of an optical fiber that is introduced into a nucleus pulposus. In the '729 patent, the distal end of a stiff optical fiber shaft extends in a lateral direction relative to a longitudinal axis of an introducer. This prevents delivery of coherent energy into the nucleus pulposus in the direction of the longitudinal axis of the introducer. Due to the limited access from the posterior lateral approach, stiff shaft and lateral energy deliver, the device of the '729 patent is unable to gain close proximity to a selected portion of the annulus (i.e., posterior, posterior medial and central posterior) requiring treatment or to precisely control the temperature at the annulus. This patent also does not teach injecting materials into the disc.

Accordingly, it is desirable to diagnose and treat disc abnormalities at locations previously not accessible via percutaneous approaches without substantial destruction to the disc. It would further be desirable to be able to administer materials to a precise, selected location within the disc, even at the posterior, posterior lateral and the posterior medial regions of the inner wall of the annulus fibrosus.

SUMMARY OF THE INVENTION

Accordingly, an object of the invention is to provide a minimally invasive method and apparatus for diagnosing and treating morphologic abnormalities of discs at selected locations within the disc.

Another object of the invention is to provide an apparatus which is advanceable and guidable along the inner wall of the annulus fibrosus.

Still a further object of the invention is to provide a device which has a distal end that is inserted into the disc and accesses the posterior, posterior lateral and the posterior medial regions of the inner wall of the annulus fibrosus in order to carry out a diagnostic or operative procedure at such a location.

These and other objects of the invention have been accomplished by providing an externally guidable intervertebral disc apparatus for manipulation of disc tissue present at a selected location of an intervertebral disc. The apparatus comprises a catheter having a distal end, a proximal end, and a longitudinal axis, the catheter having an intradiscal section at the distal end of the catheter, the intradiscal section being extendible into the disc and having sufficient rigidity to be advanceable through the nucleus pulposus and around the inner wall of the annulus fibrosus under a force applied longitudinally to the proximal end, having sufficient flexibility in a direction of the disc plane to be compliant with the inner wall, and having insufficient penetration ability to be advanceable out through the annulus fibrosus under the applied force; and a functional element located in the intradiscal section for adding or removing material at the selected location of the disc.

In addition to the apparatus, the present invention also provides methods for manipulating a disc tissue present at a selected location of an intervertebral disc, the disc having a nucleus pulposus, an annulus fibrosus, the annulus fibrosus having an inner wall, the nucleus pulposus having a diameter in a disc plane between opposing sections of the inner wall, the method comprising providing a catheter having a functional element, a distal end, a proximal end and having a longitudinal axis; applying a sufficient force to advance the catheter through the nucleus pulposus and around the inner wall of the annulus, which force is insufficient to puncture the annulus fibrosus; positioning the functional element at the selected location of the disc by advancing or retracting the catheter and optionally twisting the proximal end of the catheter; and manipulating the disc tissue at the selected location of the disc via the functional element.

BRIEF DESCRIPTION OF THE FIGURES

The invention will be better understood by reference to the following figures that form part of the current specification, wherein.

Figure 1B:
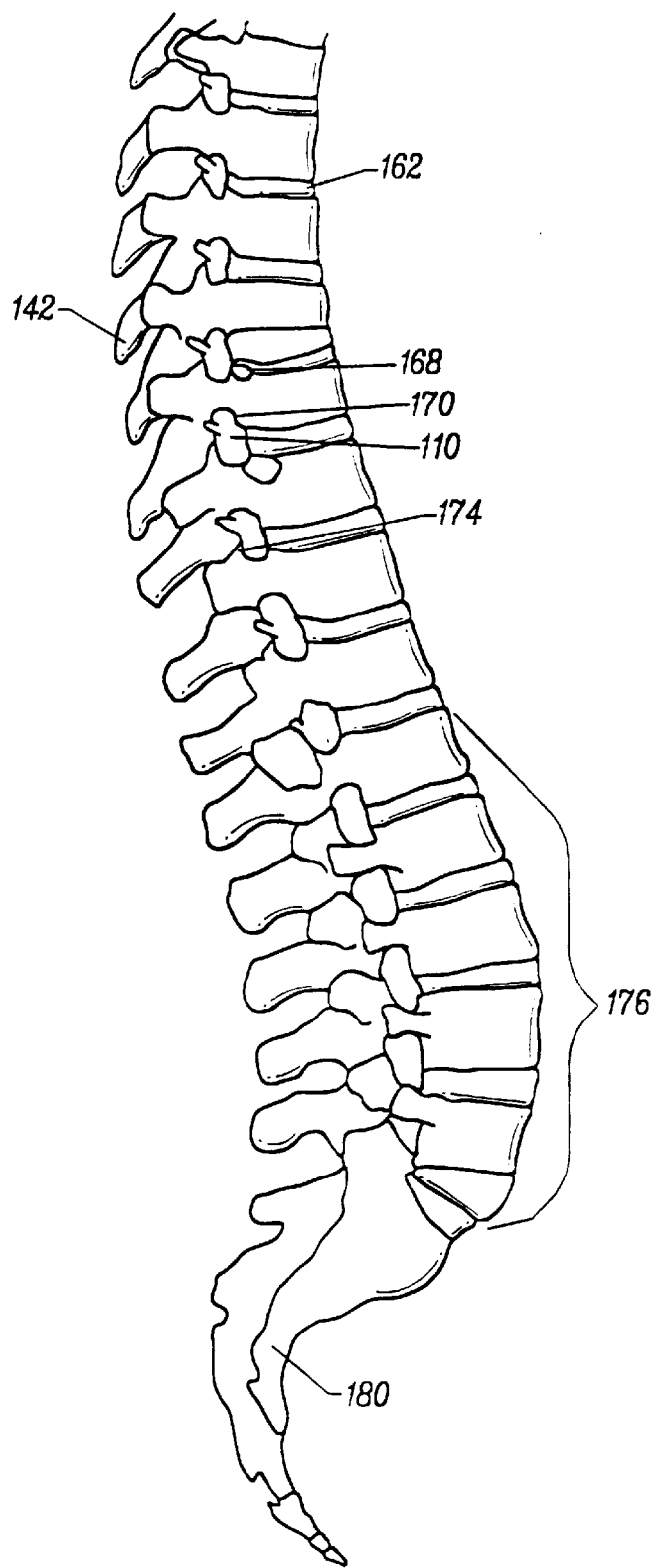
FIG. 1(b) is a lateral anatomical view of a portion of a lumbar spine.
Figure 1D:
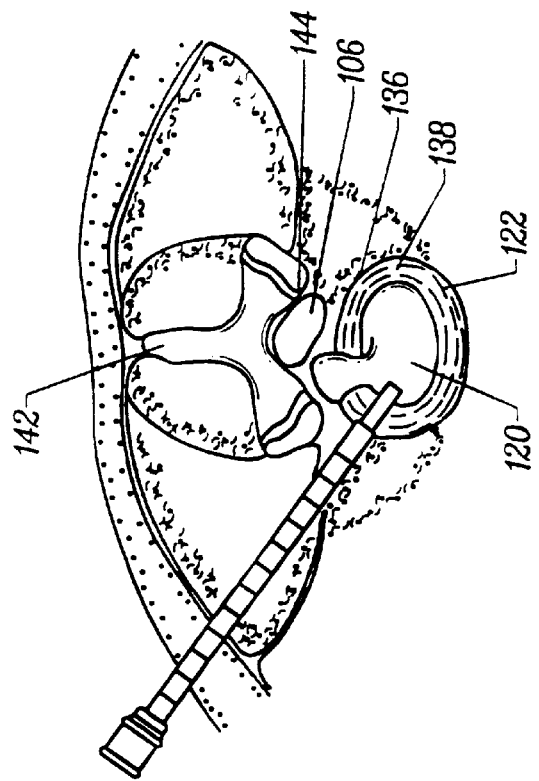
FIG. 1(d) is a superior cross-sectional anatomical view of a cervical disc and vertebra with an introducer positioned within the vertebra.
Figure 1C:
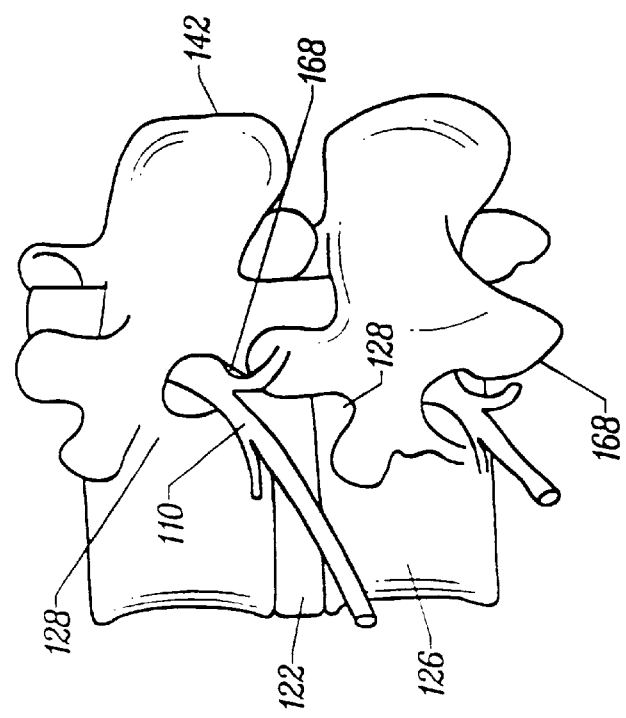
FIG. 1(c) is a posterior-lateral anatomical view of two lumbar vertebrae and illustration of the triangular working zone.

The invention now being generally described, the same will be better understood by reference to the following detailed description of specific embodiments and general features of the invention.

DETAILED DESCRIPTION

The present invention provides a method and apparatus for diagnosing and treating intervertebral disc disorders. Such disorders include but are not limited to (i) localized, acute tear or fissures in the annulus fibrosus, (ii) localized disc herniations with contained extrusions, and (iii) chronic, circumferential bulging discs.

In general, an apparatus of the invention is in the form of an externally guidable intervertebral disc apparatus for accessing and manipulating disc tissue present at a selected location of an intervertebral disc having a nucleus pulposus, an annulus fibrosus, and an inner wall of the annulus fibrosus. For ease of reference to various manipulations and distances described below, the nucleus pulposus can be considered as having a given diameter in a disc plane between opposing sections of the inner wall. This nucleus pulposus diameter measurement allows instrument sizes (and parts of instruments) designed for one size disc to be readily converted to sizes suitable for an instrument designed for a different size of disc.

The operational portion of the apparatus of the invention is brought to a location in or near the disc using techniques and apparatuses typical of percutaneous surgery. For convenience and to indicate that the apparatus of the invention can be used with any insertional apparatus that provides proximity to the disc, including many such insertional apparatuses known in the art, the term "introducer" is used to describe this aid to the method. An introducer has an internal introducer lumen with a distal opening at a terminus of the introducer to allow insertion (and manipulation) of the operational parts of the apparatus into (and in) the interior of a disc.

The operational part of the apparatus comprises an elongated element referred to as a catheter, various parts of which are located by reference to a distal end and a proximal end at opposite ends of its longitudinal axis. The proximal end is the end closest to the external environment surrounding the body being operated upon (which may still be inside the body in some embodiments if the catheter is attached to a handle insertable into the introducer). The distal end of the catheter is intended to be located inside the disc under conditions of use. The catheter is not necessarily a traditional medical catheter (i.e., an elongate hollow tube for admission or removal of fluids from an internal body cavity) but is a defined term for the purposes of this specification. "Catheter" has been selected as the operant word to describe this part of the apparatus, as the apparatus is a long flexible tube which transmits something (force, material, or otherwise) from a location external to the body to a location internal to the disc being accessed, such as a reparative adhesive. Alternatively, material can be transported in the other direction to remove material from the disc or receive sensory information. Material is removed to decrease intradiscal pressure which maintains a herniation and aggravates associated symptoms.

The catheter is adapted to slidably advance through the introducer lumen, the catheter having an intradiscal section at the distal end of the catheter, the intradiscal section being extendible through the distal opening at the terminus of the introducer into the disc. Although the length of the intradiscal portion can vary with the intended function as explained in detail below, a typical distance of extension is at least one-half the diameter of the nucleus pulposus, preferably one-half to one and one-half times the circumference of the nucleus.

In order that the functional elements of the catheter can be readily guided to the desired location within a disc, the intradiscal portion of the catheter is manufactured with sufficient rigidity to avoid collapsing upon itself while being advanced through the nucleus pulposus and navigated around the inner wall of the annulus fibrosus. The intradiscal portion, however, has insufficient rigidity to puncture the annulus fibrosus under the same force used to advance the catheter through the nucleus pulposus and then navigate around the inner wall. Absolute penetration ability will vary with sharpness and stiffness of the tip of the catheter, but in all cases a catheter of the present invention will advance more readily through the nucleus pulposus than through the annulus fibrosus.

In preferred embodiments, the intradiscal section of the catheter further has differential bending ability in two orthogonal directions at right angles to the longitudinal axis. This causes the catheter to bend along a desired plane (instead of at random). Also when a torsional (twisting) force is applied to the proximal end of the catheter, the distal end of the catheter is re-oriented in a controlled direction and permits catheter navigation in a desired plane.

A further component of the catheter is a functional element located in the intradiscal section for diagnosis or for adding or removing material at the selected location of the disc where some therapeutic action is desired. The apparatus allows the functional element to be controllably guided by manipulation of the proximal end of the catheter into a selected location for localized diagnosis and/or treatment of a diseased or injured portion of the disc.

The method of the invention, which involves manipulating a disc tissue present at a selected location of an intervertebral disc, is easily carried out with an apparatus of the invention. An introducer is provided that is located in a body so that its proximal end is external to the patient's body and the distal opening of its lumen is internal to body and (1) internal to the annulus fibrosus or (2) adjacent to an annular opening leading to the nucleus pulposus, such as an annular tear or trocar puncture that communicates with the nucleus pulposus. The catheter is then slid into position in and through the introducer lumen so that the functional element in the catheter is positioned at the selected location of the disc by advancing or retracting the catheter in the introducer lumen and optionally twisting the proximal end of the catheter to precisely navigate the catheter. By careful selection of the rigidity of the catheter and by making it sufficiently blunt to not penetrate the annulus fibrosus, and by careful selection of the flexibility in one plane versus the orthogonal plane, the distal portion of the catheter will curve along the inner wall of the annulus fibrosus as it is advanced and is selectively guided to any position within the disc. Material is then added or removed at the selected location of the disc via the functional element.

Each of the elements of the apparatus and method will now be described in more detail. However, a brief description of disc anatomy is provided first, as sizes and orientation of structural elements of the apparatus and operations of the method can be better understood in some cases by reference to disc anatomy.

The annulus fibrosus is comprised primarily of tough fibrous material, while the nucleus pulposus is comprised primarily of an amorphous colloidal gel. The border between the annulus fibrosus and the nucleus pulposus becomes more difficult to distinguish as a patient ages, beginning when a patient is approximately 30 years old, although this varies with age and often occurs at a later age. There is often a transition zone between the annulus fibrosus and the nucleus pulposus made of both fibrous-like material and amorphous colloidal gel. For purposes of this specification, the inner wall of the annulus fibrosus can include the young wall comprised primarily of fibrous material as well as the transition zone which includes both fibrous material and amorphous colloidal gels (hereafter collectively referred to as the "inner wall of the annulus fibrosus"). Functionally, that location where the catheter of the present invention encounters more resistance to penetration and bends into a radius less than that of the external wall of the annulus fibrosus is considered to be the "inner wall of the annulus fibrosus".

As with any surgical instrument and method, not all patients can be treated especially when their disease or injury is too severe. There is a medical gradation of degenerative disc disease (stages 1–5). See, for example, Adams et al., "The Stages of Disc Degeneration as Revealed by Discograms," J. Bone and Joint Surgery, 68, 36–41 (1986). As these grades are commonly understood, the methods of instrument navigation described herein would probably not be able to distinguish between the nucleus and the annulus in degenerative disease of grade 5. In any case, most treatment is expected to be performed in discs in stages 3 and 4, as stages 1 and 2 are asymptomatic in most patients, and stage 5 may require disc removal and fusion.

Figure 2:
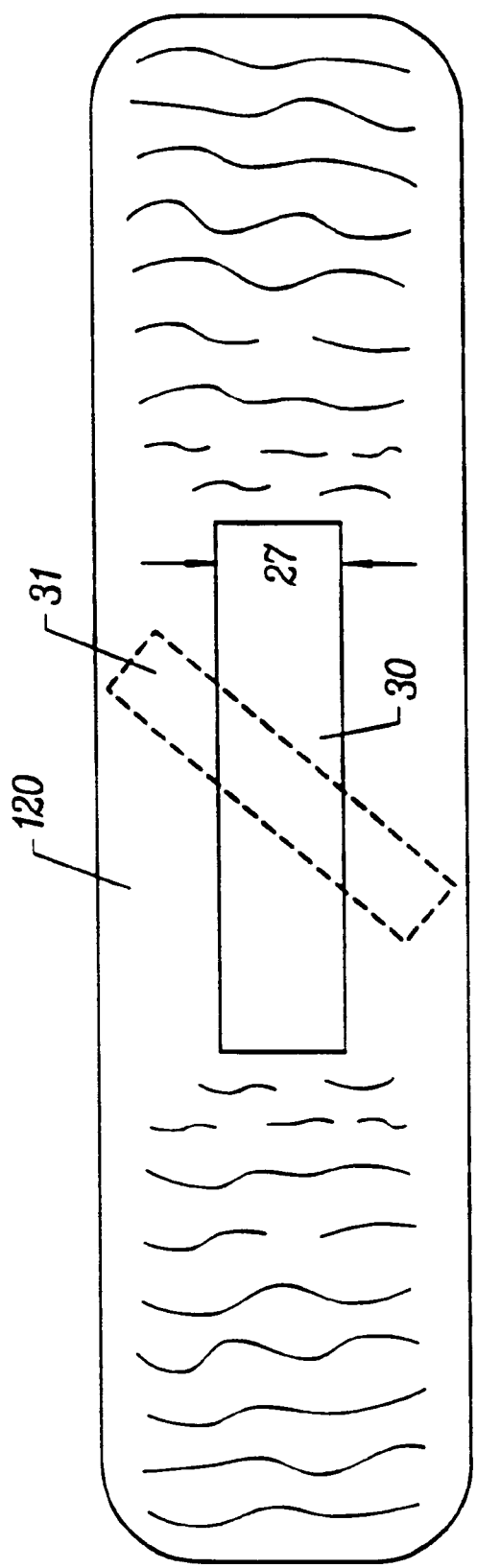
FIG. 2 is a second cross-sectional view of an intervertebral disc illustrating a disc plane of the intervertebral disc and an oblique or cephalo-caudal plane.

Some of the following discussion refers to motion of the catheter inside the disc by use of the terms "disc plane," "oblique plane" and "cephalo-caudal plane." These specific terms refer to orientations of the intervertebral disc. Referring now to FIG. 2 (which shows an axial cross-section of a disc), a disc plane 30 of the intervertebral disc is generally a plane of some thickness 27 within the nucleus pulposus 120 orthogonal to the axis formed by the spinal column (i.e., such a disc plane would be substantially horizontal in a standing human, corresponding to the "flat" surface of a vertebra. An oblique plane 31 extends along any tilted orientation relative to axial plane 30 (i.e., when tilted at 90°, such a plane would be substantially vertical in a standing human and is referred to as a cephalo-caudal plane). Reference is made to such planes to describe movements away from the disc plane. In various embodiments, disc plane 30 has a thickness no greater than the thickness of the intervertebral disc, preferably a thickness no greater than 75% of a thickness of the intervertebral disc, and more preferably a thickness no greater than 50% of a thickness of the intervertebral disc. Movement of the intradiscal portion 16 of catheter 14 is confined within a disc plane by the physical and mechanical properties of the intradiscal portion 16 during advancement of the catheter when the bending plane of the catheter is aligned with the disc plane, unless some additional force is applied to the catheter by the physician. A twisting force (which can he applied mechanically, electrically, or by any other means) acting on the proximal end of the catheter changes the forces acting on the distal end of the catheter so that the plane of the catheter bend can be angled relative to the disc plane as the catheter is advanced. Thus, the distal end of the catheter can be moved up or down (depending on the direction of the twist) within the intervertebral disc under the control of the surgeon.

Turning now to the introducer, a detailed description of an entire apparatus should not be necessary for those skilled in the art of percutaneous procedures and the design of instruments intended for such use. The method of the invention can also be carried out with endoscopic instruments, and an endoscopic apparatus having structural parts that meet the descriptions set forth in this specification would also be an apparatus of the invention.

In general, a device of the invention can be prepared in a number of different forms and can consist (for example) of a single instrument with multiple internal parts or a series of instruments that can be replaceably and sequentially inserted into a hollow fixed instrument (such as a needle) that guides the operational instruments to a selected location in or adjacent to an intervertebral disc. Because prior patents do not fully agree on how to describe parts of percutaneous instruments, terminology with the widest common usage will be used.

The introducer, in its simplest form, can consist of a hollow needle-like device (optionally fitted with an internal removable obturator or trocar to prevent clogging during initial insertion) or a combination of a simple exterior cannula that fits around a trocar. The result is essentially the same: insertion of a hollow tube (the needle or exterior cannula after removal of the plug or trocar, respectively) through skin and tissue to provide access into the annulus fibrosus. The hollow introducer acts as a guide for introducing instrumentation. More complex variations exist in percutaneous instruments designed for other parts of the body and can be applied to design of instruments intended for disc operations. Examples of such obturators are well known in the art. A particularly preferred introducer is a 17- or 18-gauge, thin-wall needle with a matched obturator, which after insertion is replaced with a catheter of the present invention.

Referring now to the figures, FIGS. 3(a) and 3(b) illustrate one embodiment of a catheter 14 of the invention as it would appear inserted into an introducer 12. The apparatus shown is not to scale, as an exemplary apparatus (as will be clear from the device dimensions below) would be relatively longer and thinner; the proportions used in FIG. 3(a) were selected for easier viewing by the reader. The distal portion of an intervertebral apparatus operates inside an introducer 12 having an internal introducer lumen 13. A flexible, movable catheter 14 is at least partially positionable in the introducer lumen 13. Catheter 14 includes a distal end selection 16 referred to as the intradiscal section, which is designed to be the portion of the catheter that will be pushed out of the introducer lumen and into the nucleus pulposus, where movement of the catheter will be controlled to bring operational portions of the catheter into the selected location within the disc. In FIG. 3(a), dashed lines are used to illustrate bending of the intradiscal portion of the catheter as it might appear under use, as discussed in detail later in the specification. FIG. 3(b) shows an end view of a handle 11 at the proximal end of the catheter, with the handle 11 having an oval shape to indicate the plane of bending, also discussed in detail later in the specification. Other sections and properties of catheter 14 are described later.

For one embodiment suitable for intervertebral discs, the outer diameter of catheter 14 is in the range of 0.2 to 5 mm, the total length of catheter 14 (including the portion inside the introducer) is in the range of 10 to 60 cm, and the length of introducer 12 is in the range 5 to 50 cm. For one preferred embodiment, the catheter has a diameter of 1 mm, an overall length of 30 cm, and an introduced length of 15 cm (for the intradiscal section). With an instrument of this size, a physician can insert the catheter for a distance sufficient to reach any selected location in the nucleus of a human intervertebral disc.

Figure 4:
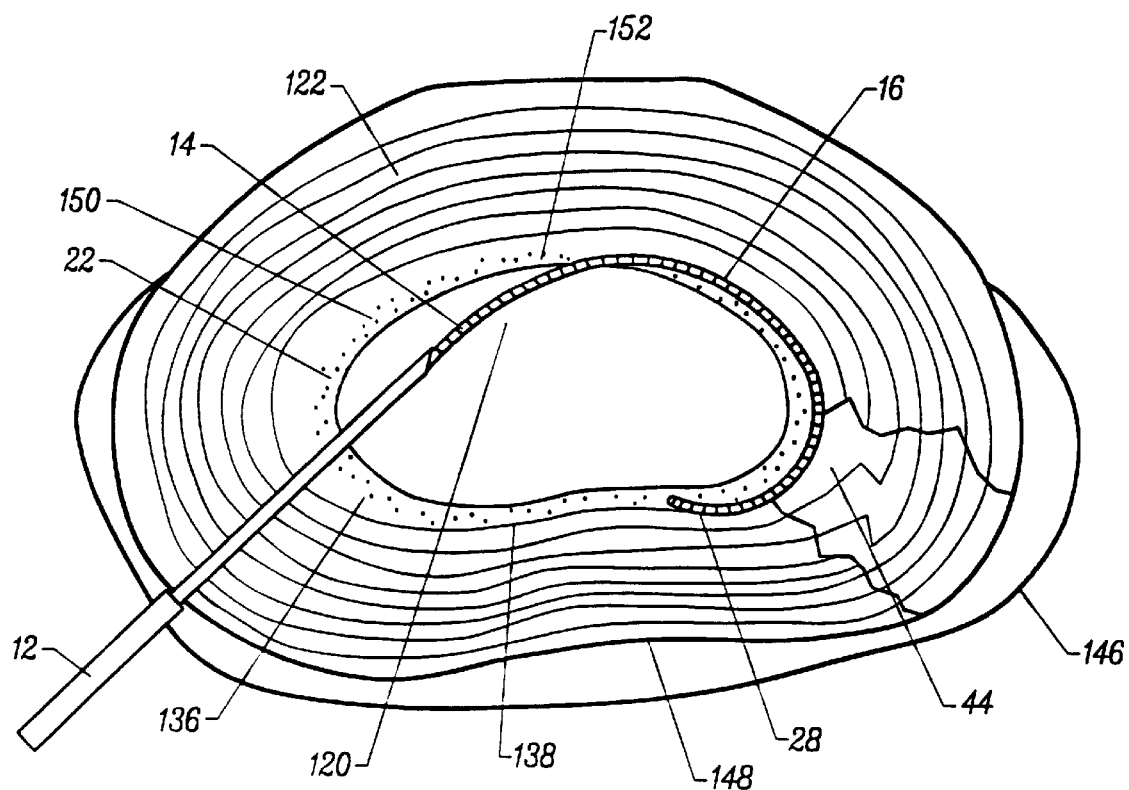
FIG. 4 is a cross-sectional view of an intervertebral disc with a portion of the intervertebral apparatus of the present invention inserted in the intervertebral disc.

FIG. 4 illustrates the anatomy of an intervertebral disc and shows an apparatus of the invention inserted into a disc. Structures of the disc are identified and described by these anatomical designations: the posterior lateral inner annulus 136, posterior medial inner annulus 138, annulus fibrosus122/nucleus pulposus 120 interface, the annulus/dural interface 146, annulus/posterior longitudinal ligament interface 148, anterior lateral inner annulus 150, and the anterior medial inner annulus 152.

Referring again to FIG. 4, the mechanical characteristics of intradiscal section 16 of catheter 14 are selected to have (1) sufficient column strength along the longitudinal axis of the catheter to avoid collapse of the catheter and (2) different flexural strengths along the two axes orthogonal to the longitudinal axis to allow controlled bending of the catheter. These parameters make the catheter conformable and guidable along inner wall 22 of an annulus fibrosus 122 to reach selected locations, such as the posterior medial annulus 138.

Specific mechanical characteristics of particular designs will be described later in the examples that follow. Generally, however, the necessary design features can be selected (in an interrelated fashion) by first providing the intradiscal section of the cannula with sufficient column strength to be advanceable through normal human nucleus pulposus material and navigable around the inner wall of the annulus fibrosus without collapse. Here "collapse" refers to bending sufficient to inhibit further advancement at the tip. Advancement of the tip is impeded by resistance from 1) the normal gelatinous nucleus pulposus, 2) denser clumps of nucleus and 3) arcing to follow the inner wall of the annulus. Column strength can be increased in many ways known in the art, including but not limited to selecting materials (e.g., metal alloy or plastic) with a high resistance to bending from which to form the catheter, forming the structure of the catheter with elements that add stiffening (such as bracing), and increasing the thickness of the structural materials. Column strength can be decreased to favor bending by selecting the opposite characteristics (e.g., soft alloys, hinging, and thin structural elements).

When the catheter collapses, the physician feels an abrupt decrease in resistance. At that time, the catheter forms one or more loops or kinks between the tip of the introducer and the distal tip of the catheter.

Particularly preferred for access to the posterior of the annulus, the tip 28 of intradiscal section 16 is biased or otherwise manufactured so that it forms a pre-bent segment prior to contact with the annulus fibrosus as shown in FIG. 3(a). The bent tip will cause the intradiscal section to tend to continue to bend the catheter in the same direction as the catheter is advanced. This enhanced curving of a pre-bent catheter is preferred for a catheter that is designed to reach a posterior region of the nucleus pulposus; however, such a catheter must have sufficient column strength to prevent the catheter from collapsing back on itself.

The intradiscal section not only must allow bending around the relatively stronger annulus fibrosus in one direction, but also resist bending in the orthogonal direction to the plane in which bending is designed to occur in. By twisting the proximal end of a catheter and thus controlling the orientation of the plane of bending while concurrently controlling the advance of the catheter into the disc nucleus, a physician can navigate the catheter and its instrumentation within the disc.

The bending stiffness of the intradiscal section as measured in Taber stiffness units (using a length of the inventive catheter as the test strip rather than the standard dimension homogeneous-material test strip) should be in the range of 2–400 units (in a 0–10,000 unit range) in the desired bending plane, preferably 3–150 units. In preferred embodiments, stiffness is in the range of 4–30 units in the desired bending plane. In all cases, the bending stiffness preferably is 2–20 times higher for bending in the orthogonal direction.

The column or compressive strength of the intradiscal section (force required to buckle a segment whose length is 25 or more times its diameter) is in the range of 0.05 to 4 kg, preferably 0.05 to 2 kg. In the most preferred embodiments, it is in the range of 0.1 to 1 kg. In the proximal shaft section (i.e., the part of the catheter proximal to the intradiscal section), this strength is in the range of 0.1 to 25 kg, preferably 0.2 to 7 kg. In the most preferred embodiments, it is in the range of 0.7 to 4 kg.

Returning now to FIG. 4, intradiscal section 16 is guidable and can reach the posterior, the posterior lateral, and the posterior medial regions of the posterior wall of the annulus fibrosus, as well as any other selected section on or adjacent to inner wall 22. In order to move the functional section of the catheter into a desired nucleus location, intradiscal section 16 is first positioned in the nucleus pulposus 120 by means of the introducer.

In most uses, introducer 12 pierces annulus fibrosus 122 and is advanced through the annulus fibrosus into the nucleus pulposus. In such embodiments, introducer 12 is then extended a desired distance into nucleus pulposus 120. Catheter 14 is advanced through a distal end of introducer 12 into nucleus pulposus 120. Advancement of the catheter 14, combined with increased resistance to advancement at the annulus fibrosus, causes the tip of the intradiscal section to bend relative to the longitudinal axis of introducer 12 when the intradiscal section approaches and contacts with the inner wall of the annulus fibrosus. Catheter 14 is navigated along inner wall 22 of annulus fibrosus 122 to any selected site of inner wall 22 or within nucleus pulposus 120. For example, intradiscal section 16 can be positioned on or adjacent to a fissure or tear 44 of annulus fibrosus 122.

The distal portion 28 of intradiscal section 16 is designed to be incapable of piercing annulus fibrosus 122. The inability of distal portion 28 to pierce the annulus can be the result of either shape of the tip 29 or column stiffness of distal portion 28, or both. The tip 29 is considered sufficiently blunt when it does not penetrate the annulus fibrosus but is deflected back into the nucleus pulposus or to the side around the inner wall of the annulus when the tip 29 is advanced. The tip can be made with a freely rotating ball. This embodiment provides not only a blunt surface but also a rolling contact to facilitate navigation.

Many percutaneous and endoscopic instruments designed for other purposes can be adapted for use in this invention. This permits different functions at the desired location after the catheter is advanced to that position. For example, cutting edges and sharp points can be present in the distal portion 28 if they can be temporarily masked by a covering element. However, such devices must sufficiently flexible and thin to meet the design characteristics described in this specification.

In another embodiment an introducer 12 pierces the skin and reaches an exterior of annulus fibrosus 122. A rigid and sharp trocar is then advanced through introducer 12 to pierce annulus fibrosus 122 and enter the disc. The trocar is then removed, and catheter 14 is advanced through a distal end of introducer 12, following the path created by the trocar in annulus fibrosus 122 beyond the end of the introducer. In such cases, the introducer is outside the annulus fibrosus 122 and only the catheter with its guidable distal portion 16 is present inside the disc. The physician can manipulate the proximal portion 15 of the catheter to move the distal portion of the catheter into a selected location for diagnosing or treating the nucleus pulposus 120 or the inner wall 22 of annulus fibrosus 122.

Figure 3:
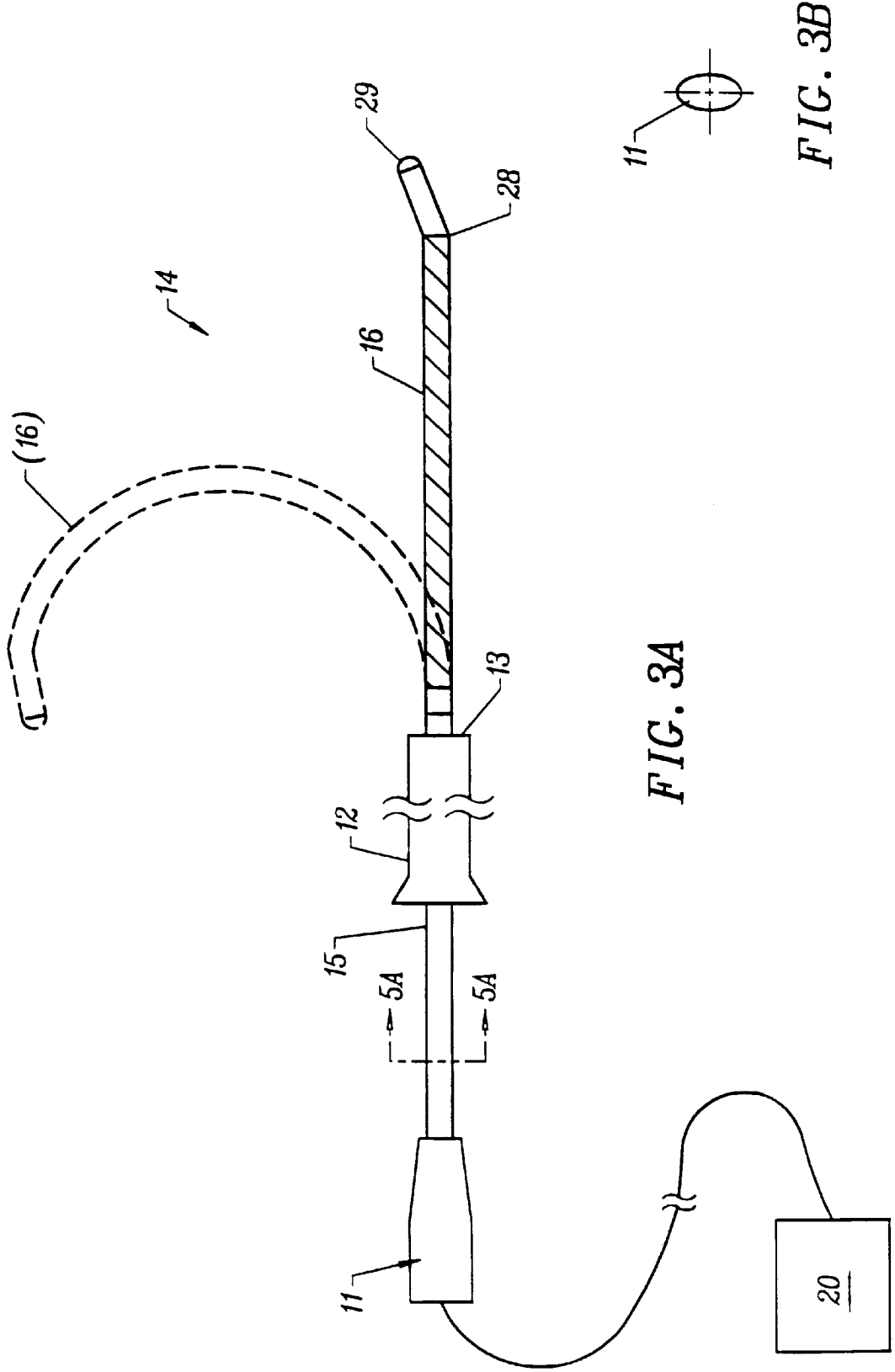
FIG. 3(a) is a plan view of an introducer and an instrument of the invention in which solid lines illustrate the position of the instrument in the absence of bending forces and dotted lines indicate the position the distal portion of the instruments would assume under bending forces applied to the tip of the instrument.
FIG. 3(b) is an end view of the handle of the embodiment shown in FIG. 3(a).

Catheter 14 is not always pre-bent as shown in FIG. 3(*a*), but optionally can include a biased distal portion 28 if desired. "Pre-bent" or "biased" means that a portion of the catheter (or other structural element under discussion) is made of a spring-like material that is bent in the absence of external stress but which, under selected stress conditions (for example, while the catheter is inside the introducer), can be held in a linear arrangement. Such a biased distal portion can be manufactured from either spring metal or superelastic memory material (such as Tinel® nickel-titanium alloy, Raychem Corp., Menlo Park Calif.). The introducer (at least in the case of a spring-like material for forming the catheter) is sufficiently strong to resist the bending action of the bent tip and maintain the biased distal portion in alignment as it passes through the introducer. Compared to unbiased catheters, a catheter with a biased distal portion 28 encourages advancement of intradiscal section 16 substantially in the direction of the bend relative to other lateral directions as shown by the bent location of intradiscal section 16 indicated by dashed lines in FIG. 3(*a*). Biasing the catheter tip also further decreases likelihood that the tip 29 will be forced through the annulus fibrosus under the pressure being used to advance the catheter.

In addition to providing a catheter tip that is biased prior to insertion into an introducer, a catheter tip can be provided that is deflected by mechanical means, such as a wire attached to one side of the tip that deflects the tip in the desired direction upon application of force to the proximal end of the deflection wire. Any device in which bending of the tip of a catheter of the invention is under control of the physician is referred to as "actively steerable." In addition to a tip that is actively steerable by action of a wire, other methods of providing a bending force at the tip can be used, such as hydraulic pressure and electromagnetic force (such as heating a shaped memory allow to cause it to contract). Any of a number of a techniques can be used to provide selective bending of the catheter in one lateral direction.

Referring now to FIG. 5(*a*), a guiding mandrel 32 can be included both to add rigidity to the catheter and to inhibit movement of catheter 14 in the inferior and superior directions while positioned and aligned in the disc plane of a nucleus pulposus 120. This aids the functions of preventing undesired contact with a vertebra and facilitating navigation. The mandrel can be flattened to encourage bending in a plane (the "plane of the bend") orthogonal to the "flat" side of the mandrel. "Flat" here is a relative term, as the mandrel can have a D-shaped cross-section, or even an oval or other cross-sectional shape without a planar face on any part of the structure. Regardless of the exact configuration, bending will preferentially occur in the plane formed by the principal longitudinal axis of the mandrel and a line connecting the opposite sides of the shortest cross-sectional dimension of the mandrel (the "thin" dimension). To provide sufficient resistance to bending of the catheter out of the desired plane while encouraging bending in the desired plane, a minimum 1.25:1 ratio of "thickest" to "thinnest" cross-sectional dimensions is required along at least a portion of the intradiscal section. The maximum ratio is 20:1, with the preferred ratio being between 1.5:1 and 16:3, more preferably between 2.5:1 and 3.5:1. These ratios are for a solid mandrel and apply to any material, as deflection under stress for uniform solids is inversely proportional to the thickness of the solid in the direction (dimension) in which bending is taking place. For other types of mandrels (e.g., hollow or non-uniform materials), selection of dimensions and/or materials that provide the same relative bending motions under stress are preferred.

A catheter of the present invention is designed with sufficient torsional strength (resistance to twisting) to prevent undesired directional movement of the catheter. Mandrels formed from materials having tensile strengths in the range set forth in the examples of this specification provide a portion of the desired torsional strength. Other materials can be substituted so long as they provide the operational functions as described herein and desired operating parameters.

While the mandrel can provide a significant portion of the column strength, selective flexibility, and torsional strength of a catheter, other structural elements of the catheter also contribute to these characteristics. Accordingly, it must be kept in mind that it is the characteristics of the overall catheter that determine suitability of a particular catheter for use in the methods of the invention. For example, a mandrel that does not have sufficient torsional strength when acting alone can be combined with another element, such as antitwisting outer sheath 40, to provide a catheter of the invention. Similarly, components inside the catheter, such as a heating element or potting compound, can be used to strengthen the catheter or provide directional flexibility at the locations of these elements along the catheter.

It is not necessary that the guiding mandrel 32 be flattened along its entire length. Different mandrels can be designed for different sized discs, both because of variations in disc sizes from individual to individual and because of variations in size from disc to disc in one patient. The bendable portion of the mandrel is preferably sufficient to allow intradiscal portion 16 of the catheter to navigate at least partially around the inner wall of the annulus fibrosus (so that the operational functions of the catheter can be carried out at any desired location along the inner wall of the annulus fibrosus). Shorter bendable sections are acceptable for specialized instruments. In most cases, a flattened distal portion of the mandrel of at least 1 cm, preferably 2 cm, is satisfactory. The flattened portion can extend as much as the entire length of the mandrel, with some embodiments being flattened for less than 13 cm, in other cases for less than 8 cm, of the distal end of the guide mandrel.

In preferred embodiments the guide mandrel or other differential bending control element is maintained in a readily determinable orientation by a control element located at the proximal end of the catheter. The orientation of the direction of bending and its amount can be readily observed and controlled by the physician. One possible control element is simply a portion of the mandrel that extends out of the proximal end of the introducer and can be grasped by the physician, with a shape being provided that enables the physician to determine the orientation of the distal portion by orientation of the portion in the hand. For example, a flattened shape can be provided that mimics the shape at the distal end (optionally made larger to allow better control in the gloved hand of the physician, as in handle 11 of FIG. 3(b)). More complex proximal control elements capable of grasping the proximal end of the mandrel or other bending control element can be used if desired, including but not limited to electronic, mechanical, and hydraulic controls for control by the physician.

The guide mandrel can also provide the function of differential flexibility by varying the thickness in one or more dimensions (for example, the "thin" dimension, the "thick" dimension, or both) along the length of the mandrel. A guide mandrel that tapers (becomes gradually thinner) toward the distal tip of the mandrel will be more flexible and easier to bend at the tip than it is at other locations along the mandrel. A guide mandrel that has a thicker or more rounded tip than more proximal portions of the mandrel will resist bending at the tip while encouraging bending to occur at more proximal locations. Thickening (or thinning) can also occur in other locations along the mandrel. Control of the direction of bending can be accomplished by making the mandrel more round, i.e., closer to having 1:1 diameter ratios; flatter in different sections of the mandrel; or by varying the absolute dimensions (increasing or decreasing the diameter). Such control over flexibility allows instruments to be designed that minimize bending in some desired locations (such as the location of connector of an electrical element to avoid disruption of the connection) while encouraging bending in other locations (e.g., between sensitive functional elements). In this manner, a catheter that is uniformly flexible along its entire length, is variably flexibility along its entire length, or has alternating more flexible and less flexible segments, is readily obtained simply by manufacturing the guide mandrel with appropriate thickness at different distances and in different orientations along the length of the mandrel. Such a catheter will have two or more different radii of curvature in different segments of the catheter under the same bending force.

In some preferred embodiments, the most distal 3 to 40 mm of a guide mandrel is thinner relative to central portions of the intradiscal section to provide greater flexibility, with more the proximal 10 to 40 cm of the intradiscal section being thicker and less flexible to add column strength and facilitate navigation.

The actual dimensions of the guide mandrel will vary with the stiffness and tensile strength of the material used to form the mandrel. In most cases the mandrel will be formed from a metal (elemental or an alloy) or plastic that will be selected so that the resulting catheter will have characteristics of stiffness and bending that fall within the stated limits. Additional examples of ways to vary the stiffness and tensile strength include transverse breaks in a material, advance of the material so that it "doubles up," additional layers of the same or different material, tensioning or relaxing tension on the catheter, and applying electricity to a memory metal.

Figure 5A:
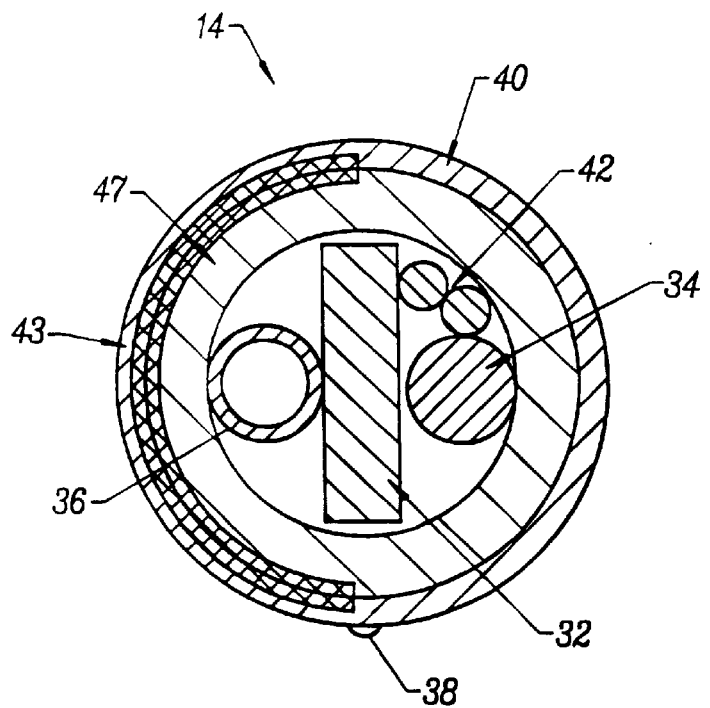
FIG. 5(a) is a cross-sectional view of the intervertebral segment of the embodiment of the invention shown in FIG. 3(a) taken along the line 5(a)—5(a) of FIG. 3(a).
Figure 5B:
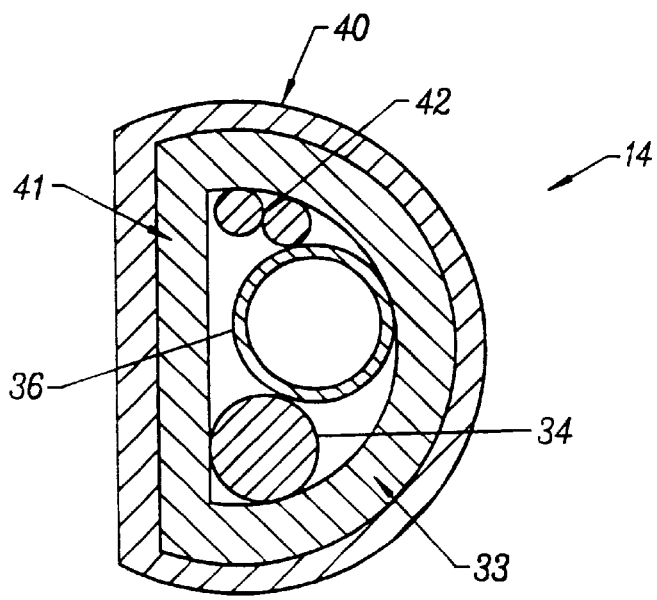
FIG. 5(b) is a cross-sectional view of the intervertebral segment of a second embodiment of the present invention having a combined wall/guiding mandrel.

As illustrated in FIG. 5(b), in some embodiments of an apparatus of the invention, guiding mandrel 32 is combined with at least a portion of the catheter 14 to form a structure which provides the functions of both, a wall/mandrel 41. In this figure, the wall/mandrel 41 can be varied in dimensions as described in the previous section of this specification directed to a separate mandrel, with the same resulting changes in function. For example, changing the thickness of the wall/mandrel 41 that functions as the mandrel portion changes the flexibility and preferred direction of bending of the catheter. In many cases, the wall/mandrel 41 will be thinner than other portions of the catheter wall 33 so that wall/mandrel 41 controls bending. Alternatively, wall/mandrel 41 can be formed of a different material than the other portions 33 of the catheter walls (i.e., one with a lower tensile and/or flexural strength) in order to control bending.

Returning now to FIG. 5(a), the guiding mandrel 32 is generally located in the interior of catheter 14, where it shares space with other functional elements of the catheter. For example, functional element lumen 34 can receive any of a variety of different couplings from an external source 20 to a functional element port further along the catheter, including but not limited to a wire or other apparatus for transmitting force to a mechanical element. Additionally, functional element lumen 34 can house a surgical instrument 18. Alternatively or concurrently hollow lumen(s) for delivery and/or removal of a fluid can be present. No limitation should be placed on the types of force, equipment or material transporting elements present in the catheter. These are merely some of the possible alternative functional elements that can be included in the intradiscal portion of the catheter. Accordingly, a general description will now be given of some of the possible functional elements.

Since the purpose of the inventive catheter is to perform some function on disc or nearby tissue by operation of the instrument at a user-selected location adjacent to or inside the disc, a functional element is provided in or on the catheter to carry out that purpose.

Non-limiting examples of functional elements include any element capable of aiding diagnosis, delivering or removing a material from a location adjacent the element's location in the catheter, such as an opening in the catheter for delivery of a fluid or for suction, a mechanical grasping tool for removing or depositing a solid, a cutting tool (which includes all similar operations, such as puncturing), a sensor for measurement of a function (such as electrical resistance, temperature, or mechanical strength), or a functional element having a combination of these functions.

The functional element can be at any location in the intradiscal portion of the catheter, depending on its intended use. Multiple functional elements can be present, either multiple functional elements of different types (e.g., fluid port and a temperature sensor) or multiple functional elements of the same type (e.g., multiple independent fluid ports spaced along the intradiscal portion).

Some embodiments have an interior infusion lumen 36. Infusion lumen 36 is configured to transport a variety of different mediums including but not limited to electrolyte solutions (such as normal saline), contrast media, pharmaceutical agents (such as corticosteroid or nonsteroidal anti-inflammatory agents), disinfectants, filling or binding materials such as collagens or cements, chemonucleolytic agents and the like, from a reservoir exterior to the patient to a desired location within the interior of a disc. Further, infusion lumen 36 can be used as an aspiration lumen to remove nucleus material or excess liquid or gas (naturally present, present as the result of a liquefying operation, or present because of prior introduction) from the interior of a disc. When used to transport a fluid for irrigation of the location in the disc where some action is taking place (such as ablation, which generates waste materials), the infusion lumen is sometimes referred to as an irrigation lumen. Infusion lumen 36 can be coupled to medium reservoir 21 through the catheter (see FIG. 3(a)).

Included in the embodiment shown in FIG. 5(a) is one or more sensor lumens 42. An example is a wire connecting a thermal sensor at a distal portion of the catheter to control elements attached to the proximal handle 11 of the catheter. Mechanical or hydraulic elements can also function as to transport force from one location of the catheter to another and thus to control or provide feedback from functional elements at remote locations.

In one embodiment, catheter intradiscal section 16 and/or distal portion 28 are positionable to any selected site around and/or adjacent to inner wall 22 of annulus fibrosus 122 for the delivery of therapeutic and/or diagnostic agents including but not limited to electrolyte solutions, contrast media, pharmaceutical agents, disinfectants, collagens, cements, and chemonucleolytic agents. Intradiscal section 16 is navigational and can reach the posterior, the posterior lateral, and the posterior medial regions of the posterior wall of the annulus fibrosus, as well as any selected section on or adjacent to inner wall 22. In a preferred embodiment, intradiscal section 16 is positioned along the posterior lateral wall of the intervertebral disc, along the anterior lateral wall of the intervertebral disc, or along the anterior medial wall of the intervertebral disc, as it is steerable and can be positioned at any of the above-mentioned sites. In a preferred embodiment, intradiscal section 16 is positioned adjacent to the entire posterior wall of the disc. Sufficient material such as a bio-filler can then be delivered, for example, to seal a fissure in the posterior annulus.

In a preferred embodiment of FIG. 5(*a*), markings 38 are visible on the portion of the catheter that is located during normal operation outside the body being acted upon, particularly for embodiments in which the proximal end of the catheter is designed to be directly manipulated by the hand of the physician. Advancement of the catheter into the introducer will advance the markings into the introducer, thereby showing how far the catheter has been advanced into the nucleus. Such a visible marking 38 can be positioned on an exterior surface of the catheter or can be present on an interior surface and visible through a transparent outer covering or sheath. Preferred are visible markings every centimeter to aid the physician in estimating the catheter tip advancement.

If desired, visible markings can also be used to show twisting motions of the catheter to indicate the orientation of the bending plane of the distal portion of the catheter. It is preferred, however, to indicate the distal bending plane by the shape and feel of the proximal end of the catheter assembly. The catheter can be attached to or shaped into a handle 11 that fits the hand of the physician and also indicates the orientation of the distal bending plane. Both the markings and the handle shape thus act as control elements to provide control over the orientation of the bending plane; other control elements, such as plungers or buttons that act on mechanical, hydrostatic, electrical, or other types of controls, can be present in more complex embodiments of the invention.

Additionally, a radiographically opaque marking device can be included in the distal portion of the catheter (such as in the tip or at spaced locations throughout the intradiscal portion) so that advancement and positioning of the intradiscal section can be directly observed by radiographic imaging. Such radiographically opaque markings are preferred when the intradiscal section is not clearly visible by radiographic imaging, such as when the majority of the catheter is made of plastic instead of metal. A radiographically opaque marking can be any of the known (or newly discovered) materials or devices with significant opacity. Examples include but are not limited to a steel mandrel sufficiently thick to be visible on fluoroscopy, a tantalum/polyurethane tip, a gold-plated tip, bands of platinum or gold, and soldered spots of gold and polymeric materials with radio-opaque filler, such as barium sulfate.

A sheath 40 can optionally be positioned around catheter 14. Sheath 40 provides a flexible surface that is smooth and provides for easy introduction into a selected area within the disc. Sheath 40 can be made of a variety of different materials including but not limited to polyester, rayon, polyimide, polyurethane, polyethylene, polyamide and silicone. When visible markings are present to indicate the advancement of the catheter, either the sheath carries the markings, or the sheath is clear to reveal markings underneath.

Figure 6:
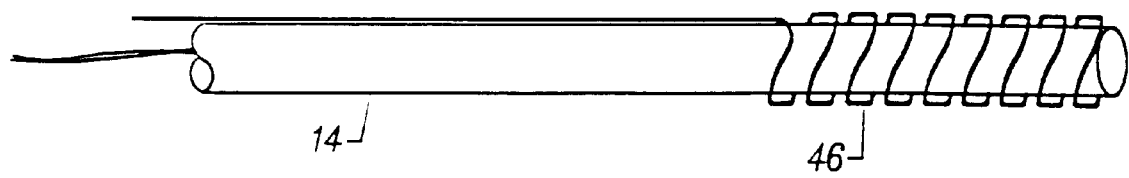
FIG. 6 is a partial cross-sectional view of an embodiment an apparatus of the invention illustrating a sensor positioned in an interior of the intradiscal section of the catheter.

In the embodiment illustrated in FIG. 6, a thermal sensor 48 may be position in an interior location of catheter 14. In another embodiment, thermal sensor 48 is positioned on an exterior surface of catheter 14. A thermal sensor can be used to measure the amount t of thermal energy released by a cement which is curing. If too much heat is generated, the application of more cement can be slowed or cool irrigating solution can be applied to the area. A potting material can be used to fix the position of thermal sensor 48 and provide a larger area from which to average the measured temperature. Thermal sensor 48 is of conventional design, including but not limited to a thermistor, T type thermocouple with copper constantan, J type, E type, K type, fiber optics, resistive wires, thermocouple, IR detectors, and the like. Optionally, there may be a lumen 42 for the thermal sensor connection.

Figure 7:
FIG. 7 is a partial perspective view of an intradiscal section of the catheter having a helical structural element to prevent twisting.

In the embodiment illustrated in FIG. 7, catheter 14 can be prepared with a wound helical structural element 49 to increase flexibility and minimize kinking. In this figure, multiple, spaced-apart structural elements 50 are shown which could have (for example) ports through which a material is delivered. However, other structures and geometries are suitable for catheter 14, including but not limited to a substantially smooth surface (and specifically including the devices using an internal guide mandrel as previously described). For example, a sheath can be provided over the functional element lumen, and the guiding mandrel inside the coil can be encapsulated in silicone potting material. The tubing flexibility and the silicone potting material prevent kinking. Catheter 14 may both be entirely or only partially disposable. Catheter 14 can be sterilized.

In a preferred embodiment of the invention, the materials that make up the various parts of an apparatus of the invention have the following characteristics: The guiding mandrel should have a tensile strength of about 600 to 2100 MPa, a height in the range of 0.2 to 2.032 mm and a width in the range of 0.05 to 0.5 mm. The plastic sheath should elongate at least 25%, melt at a temperature no lower than 80° C. and have a thickness in the range of 0.05 to 0.2 mm. Tensile strength and % elongation can be measured according to ASTME8 (tension test of metallic materials).

Degenerative discs with fissures or tears can be treated non-destructively without the removal of disc tissue, other than limited desiccation of the nucleus pulposus which reduces its water content. Fissures can also be repaired by injecting sealants such as bonding material (adhesives and cements) or filler (nonadhesive material that blocks the opening) that help seal the fissure. Collagen from a variety of sources can be used (e.g., bovine extracted collagen from Semex Medical, Frazer Pa., or human recombinant collagen from Collagen Corp., Palo Alto, Calif.). The collagen is injected dissolved or as a fine slurry.

A variety of different biomaterials can also be delivered to the disc via the inventive catheter, including but not limited to irrigation (electrolyte) solutions, contrast media (Conray meglumine iothalamate), pharmaceutical agents (e.g., corticosteroids, like methylprednisolone sodium succinate (Pharmacia Upjohn, Kalamazoo, Mich.) and nonsteroidal anti-inflammatory drugs), chemonucleolytic agents (e.g., chymopapain), hydrogel, osteoinductive materials (e.g., BMP as disclosed in U.S. Pat. No. 5,364,839), chondrocyte-inductive material (e.g., TGF-β) and the like. The materials are delivered by the introducer to the disc space or through the catheter if it has a hollow lumen. Preferably, however, when precision placement of the material (as in a fissure) is necessary or desired, the preferred delivery method uses the apparatus described above, especially when delivery to the posterior, posterior lateral, or posterior medial region of the disc is desired.

The materials are delivered in an amount sufficient to effect treatment (e.g., to decrease the extent of a fissure at least partially, preferably to fill a fissure completely). The delivered material can be fixed in position by injecting an adhesive, a combination of thrombin and fibrinogen, or a hydrogel which is liquid at room temperature but gels at body temperature.

By way of example, to seal a fissure, a combination of thrombin and fibrinogen is injected via the inventive catheter to the site of the fissure, which the mixture coagulates and seals the annulus. A kit with appropriate syringes and other equipment is available from Micromedics, Inc., Eagan Minn. Frozen fibrinogen solution is thawed in its storage bag and then dispensed to a small med cup. Thrombin is reconstituted with sterile water in the "slow gel" concentration (100 units/ml) for tissue bonding. For example, 100 ml is added to a vial containing 10,000/Thrombin solution is withdrawn from the vial and dispensed to a second med cup. Two syringes are filled equally, one with each solution. Then the syringe tips are each twisted into an applicator that mixes the solutions before passing the mixture to an administration tube. The syringes are fitted into the dual syringe holder and the plunger link, which helps the practitioner administer equal amounts of thrombin and fibrinogen. Then the practitioner connects the administration tube to the proximal end of the inventive catheter, depresses the plungers and dispenses the sealant solution to the fissure. The thrombin and fibrinogen react and form a natural seal over the fissure.

Chymopapain can be injected through the subject catheter, particularly near a herniation of the disc. Chymopapain works by splitting side chains off the proteoglycan molecules, thereby decreasing their ability to hold water and decreasing their volume. The disc gradually decreases in size. A typical dose is 0.75 to 1.0 ml (2000 pKat/ml).

All publications and patent applications mentioned in this specification are herein incorporated by reference to the same extent as if each individual publication or patent application was specifically and individually indicated to be incorporated by reference.

The foregoing description of preferred embodiments of the invention has been presented for purposes of illustration and description. It is not intended to be exhaustive or to limit the invention to the precise forms disclosed. Many modifications and variations will be apparent to practitioners skilled in this art. It is intended that the scope of the invention be defined by the following claims and their equivalents.

What is claimed is:

1. An externally guidable intervertebral disc apparatus having a longitudinal axis comprising:
    a proximal end for externally guiding the distal end of the apparatus within an intervertebral disc; and
    a self-navigating intradiscal section adjacent a distal end of the apparatus which navigates itself adjacent an inner wall of an annulus of the disc when the apparatus is extended into the intervertebral disc, the intradiscal section having (a) sufficient rigidity to be advanceable through a nucleus pulposus and around the inner wall of an annulus fibrosus under a force applied longitudinally to the proximal end of the apparatus, (b) insufficient penetration ability to be advanceable out through the annulus fibrosus under the applied force, and (c) sufficient flexibility in a direction of a disc plane to be compliant with the inner wall.

2. The apparatus of claim 1, wherein at least a portion of the intradiscal section further has differential bending ability in two orthogonal directions at right angles to the longitudinal axis.

3. The apparatus of claim 2, wherein the differential bending ability is controlled by a structural element with different thicknesses in the two orthogonal directions.

4. The apparatus of claim 3, wherein the different thicknesses are maintained in a fixed orientation relative to the catheter by a control element located at the proximal end of the apparatus.

5. The apparatus of claim 2, wherein the intradiscal section of the apparatus has one or more flat sides.

6. The apparatus of claim 1, wherein the apparatus further comprises an introducer which provides access to the disc and through which the apparatus slidably advances.

7. The apparatus of claim 1, wherein the intradiscal section has a length at least one-half of the diameter of the nucleus pulposus.

8. The apparatus of claim 1, wherein the distal end has a blunt tip.

9. The apparatus of claim 1, wherein the intradiscal section has a tip less rigid than a more proximal portion of the intradiscal section.

10. The apparatus of claim 1, wherein the intradiscal section has a directionally biased tip portion.

11. The apparatus of claim 1, wherein at least a portion of the intradiscal section of the apparatus is actively steerable.

12. The apparatus of claim 1, wherein at least a portion of the apparatus is radiographically opaque.

13. The apparatus of claim 1, wherein the intradiscal section of the apparatus includes a wound helical support structure.

14. The apparatus of claim 1, wherein the intradiscal section of the apparatus is configured to have at least two radii of curvature when advanced through the nucleus pulposus and around the inner wall of the annulus fibrosus.

15. The apparatus of claim 1, wherein the intradiscal section has at least one sensor capable of monitoring temperature.

16. The apparatus of claim 1, wherein a distal tip of the distal end of the apparatus has a rolling ball tip.

17. The apparatus of claim 1, wherein the intradiscal section has a bending stiffness as measured in Taber stiffness units between about 2–400 units in a desired bending plane.

18. The apparatus of claim 1, wherein the intradiscal section has a bending stiffness as measured in Taber stiffness units between about 3–150 units in a desired bending plane.

19. The apparatus of claim 1, wherein the intradiscal section has a bending stiffness as measured in Taber stiffness units between about 4—30 units in a desired bending plane.

20. The apparatus of claim 19, wherein the proximal end of the apparatus has a column strength between about 0.2–7 kg.

21. The apparatus of claim 19, wherein the proximal end of the apparatus has a column strength between about 0.7–4 kg.

22. The apparatus of claim 1, wherein the intradiscal section has a column strength between about 0.05–4 kg.

23. The apparatus of claim 22, wherein the proximal end of the apparatus has a column strength between about 0.1–25 kg.

24. The apparatus of claim 22, wherein the proximal end of the apparatus has a column strength between about 0.2–7 kg.

25. The apparatus of claim 22, wherein the proximal end of the apparatus has a column strength between about 0.7–4 kg.

26. The apparatus of claim 1, wherein the intradiscal section has a column strength between about 0.05–2 kg.

27. The apparatus of claim 26, wherein the proximal end of the apparatus has a column strength between about 0.1–25 kg.

28. The apparatus of claim 26, wherein the proximal end of the apparatus has a column strength between about 0.2–7 kg.

29. The apparatus of claim 26, wherein the proximal end of the apparatus has a column strength between about 0.7–4 kg.

* * * * *

UNITED STATES PATENT AND TRADEMARK OFFICE
CERTIFICATE OF CORRECTION

PATENT NO.    : 6,099,514
DATED         : August 8, 2000
INVENTOR(S)   : Sharkey et al.

Figure 1A:
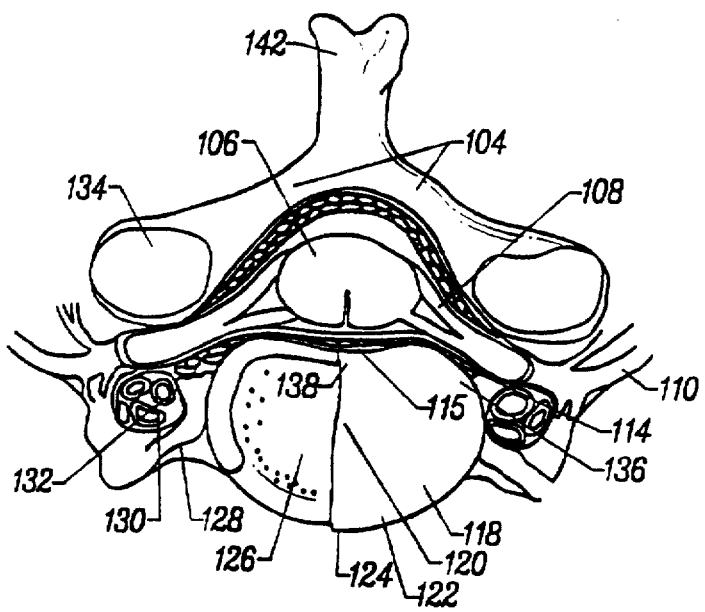
FIG. 1(a) is a superior cross-sectional anatomical view of a cervical disc and vertebra.
Figure 1B:
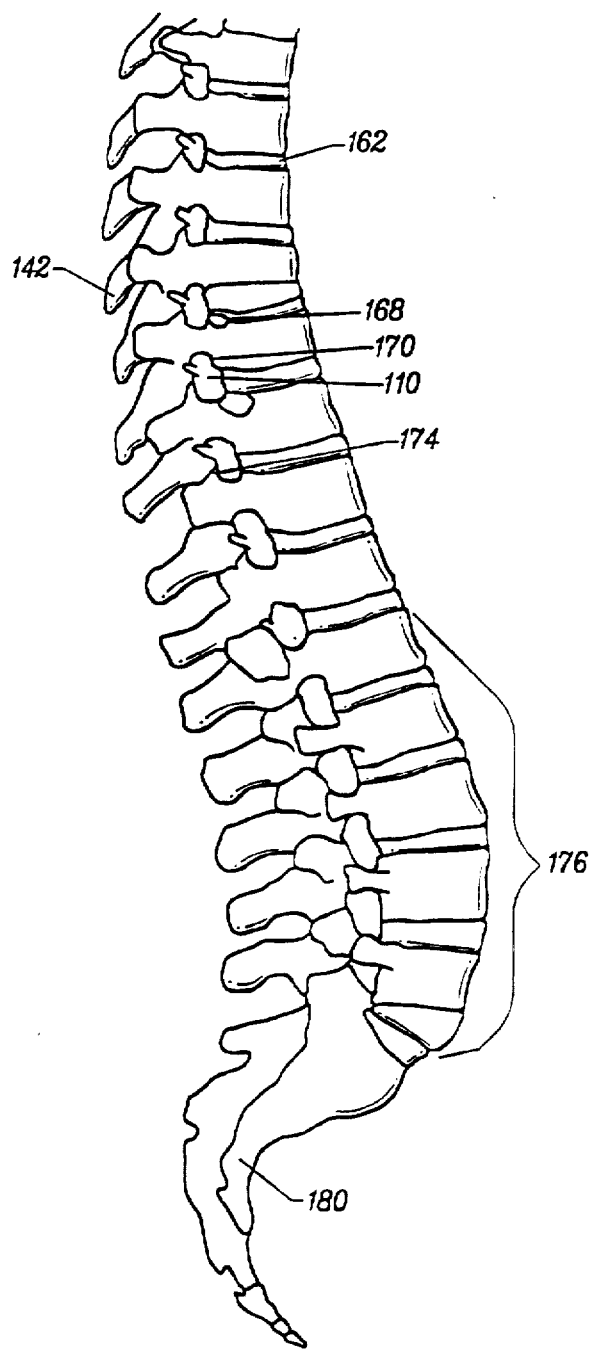

It is certified that error appears on the above-identified patent and that said Letters Patent are hereby corrected as shown below:

In the drawings, please substitute the attached Figure 1A as sheet 1 of 8 and insert Figure 1B as sheet 2 of 8.

Signed and Sealed this

Seventeenth Day of April, 2001

*Attest:*

NICHOLAS P. GODICI

*Attesting Officer*    *Acting Director of the United States Patent and Trademark Office*

UNITED STATES PATENT AND TRADEMARK OFFICE
CERTIFICATE OF CORRECTION

PATENT NO.    : 6,099,514
DATED         : August 8, 2000
INVENTOR(S)   : Sharkey et al.

It is certified that error appears in the above-identified patent and that said Letters Patent is hereby corrected as shown below:

<u>Title page,</u>
After item [22], add --

[63] Divisional of U.S. Application Ser. No. 08/881,527, filed Jun. 24, 1997, now U.S. Patent No. 5,980,504, a continuation-in-part of U.S. Application Ser. No. 09/153,552, filed Sep. 15, 1998, now U.S. Patent No. 6,126,682, and a continuation-in-part of U.S. Application No. 08/881,525, now U.S. Patent No. 6,122,549, U.S. Application No. 08/881,692, now U.S. Patent No. 6,073,051, U.S. Application No. 08/881,693, now U.S. Patent No. 6,007,570, U.S. Application No. 08/881,694, now U.S. Patent No. 6,095,149, each filed June 24, 1997. --

Signed and Sealed this

Sixteenth Day of July, 2002

Attest:

Attesting Officer

JAMES E. ROGAN
Director of the United States Patent and Trademark Office